(12) United States Patent
Bungo

(10) Patent No.: US 6,408,684 B1
(45) Date of Patent: Jun. 25, 2002

(54) DETECTION DEVICE FOR APPARATUS FOR ANALYSIS

(75) Inventor: Hajime Bungo, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/488,901

(22) Filed: Jan. 21, 2000

(30) Foreign Application Priority Data

Mar. 31, 1999 (JP) ............................................ 11-090853

(51) Int. Cl.[7] ......................... G01N 31/08; G01N 30/86; G06F 15/20; B01D 15/08
(52) U.S. Cl. ..................... 73/61.61; 73/61.57; 73/23.21; 73/23.23; 210/198.2; 702/88; 702/89
(58) Field of Search ............................... 73/61.61, 61.52, 73/61.57, 23.21, 23.23, 23.36; 702/87–89; 210/198.2

(56) References Cited

U.S. PATENT DOCUMENTS

| | | | | |
|---|---|---|---|---|
| 3,359,410 A | * | 12/1967 | Frisby et al. | 235/183 |
| 3,381,519 A | * | 5/1968 | Ashmead et al. | 73/23.1 |
| 3,555,260 A | * | 1/1971 | Karohl | 235/183 |
| 3,590,628 A | * | 7/1971 | Orr | 73/23.1 |
| 4,357,668 A | * | 11/1982 | Schwartz et al. | 364/497 |
| 4,837,726 A | * | 6/1989 | Hunkapiller | 364/498 |
| 4,875,169 A | * | 10/1989 | Synovec | 364/497 |
| 4,927,532 A | * | 5/1990 | Pospisil et al. | 210/198.2 |
| 5,311,444 A | * | 5/1994 | Ohta | 364/497 |
| 5,592,402 A | * | 1/1997 | Beebe et al. | 364/578 |
| 6,076,047 A | * | 6/2000 | Ito et al. | 702/32 |
| 6,112,161 A | * | 8/2000 | Dryden et al. | 702/85 |

* cited by examiner

Primary Examiner—Hezron Williams
Assistant Examiner—David J. Wiggins
(74) Attorney, Agent, or Firm—Beyer Weaver & Thomas LLP

(57) ABSTRACT

A detection device for an apparatus for carrying out analysis such as a chromatograph includes not only a detector for outputting detection signals but also a stabilization judging unit for measuring drift and noise of these detection signals over time and automatically transmitting a start signal which permits the apparatus for analysis to start its operations when the measured drift becomes smaller than a standard drift value such as one-tenth of the optical absorbance measured for a spectrum of an analyzed sample at the detection wavelength. A standard noise value setting unit may be further provided for receiving detection signals at detection wavelength while a standard sample is placed inside a detection cell, calculating a standard noise value on the basis of intensity of the detection signals, and transmitting the calculated standard noise value to the stabilization judging unit. A standard drift value setting unit may also be further provided in the case of a chromatograph with a column for storing standard drift values corresponding to measured temperature of the column when measurements are taken by the chromatograph and transmitting the retrieved drift value to the stabilization judging unit.

12 Claims, 6 Drawing Sheets

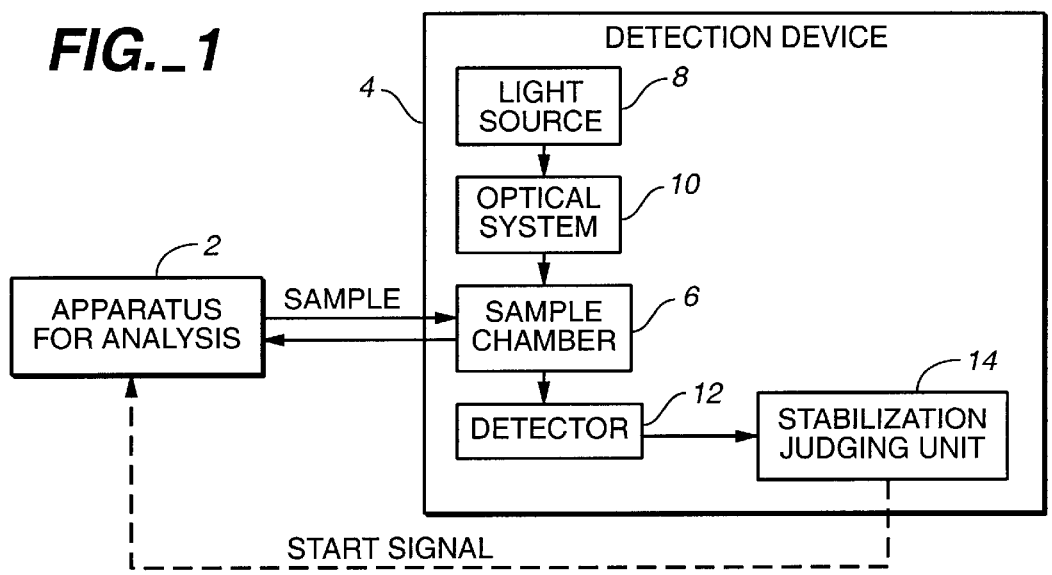
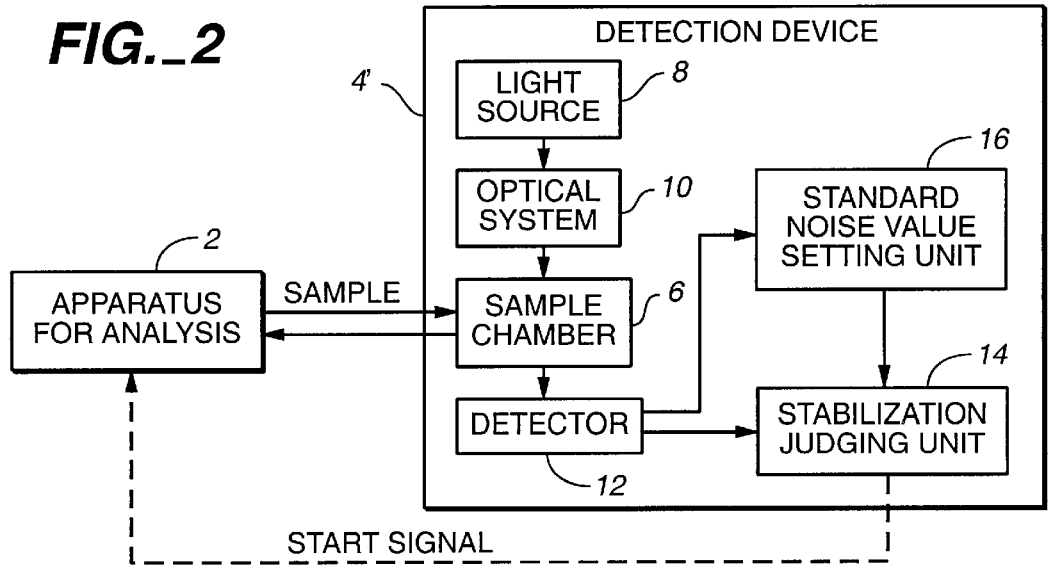

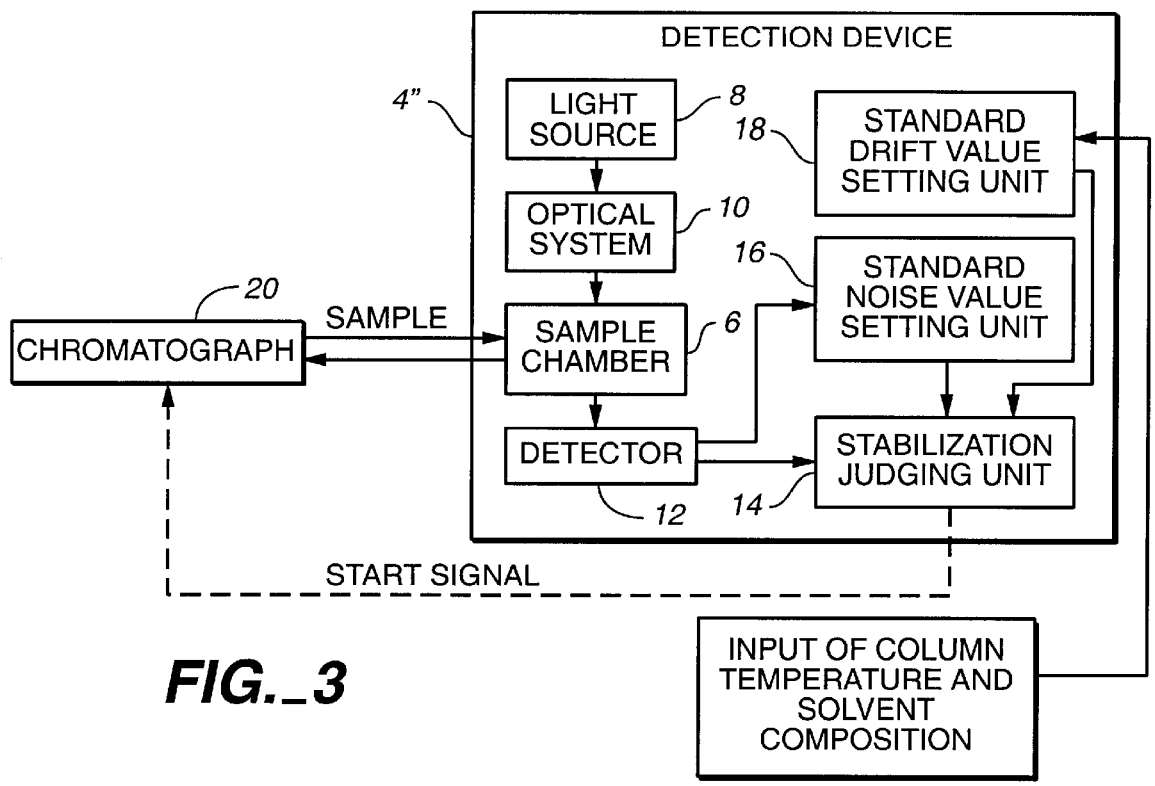
FIG._3
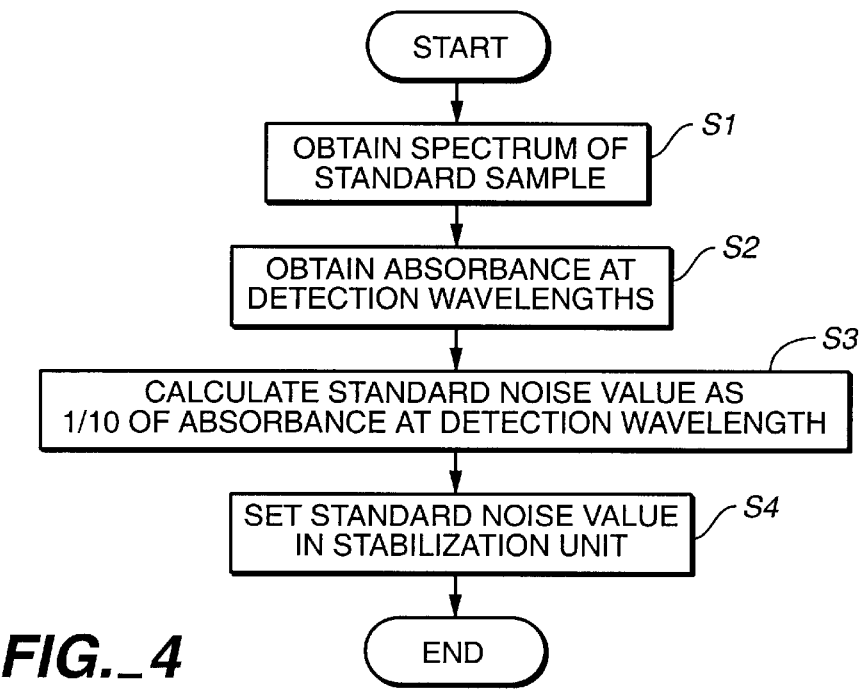
FIG._4

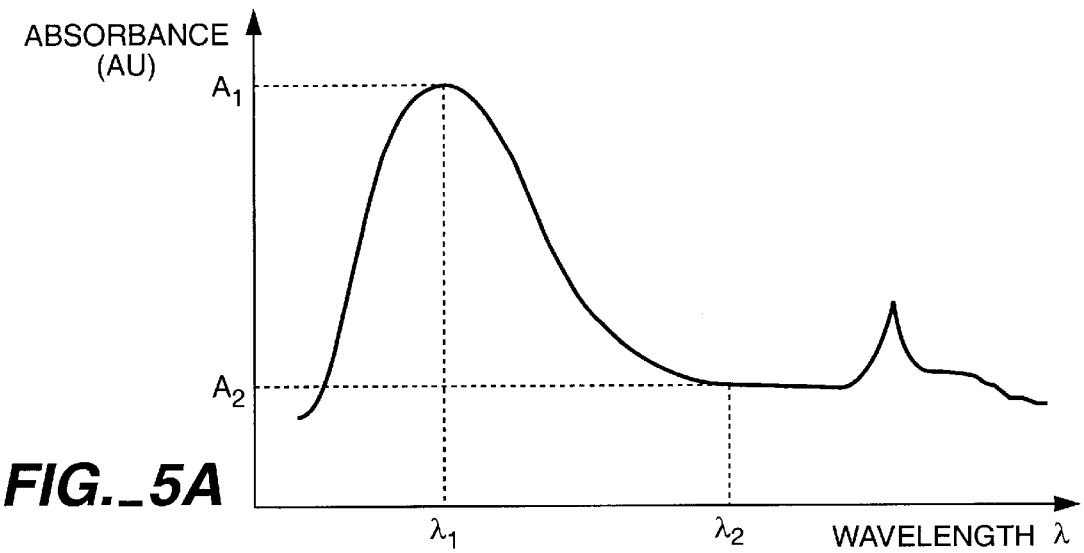
FIG._5A
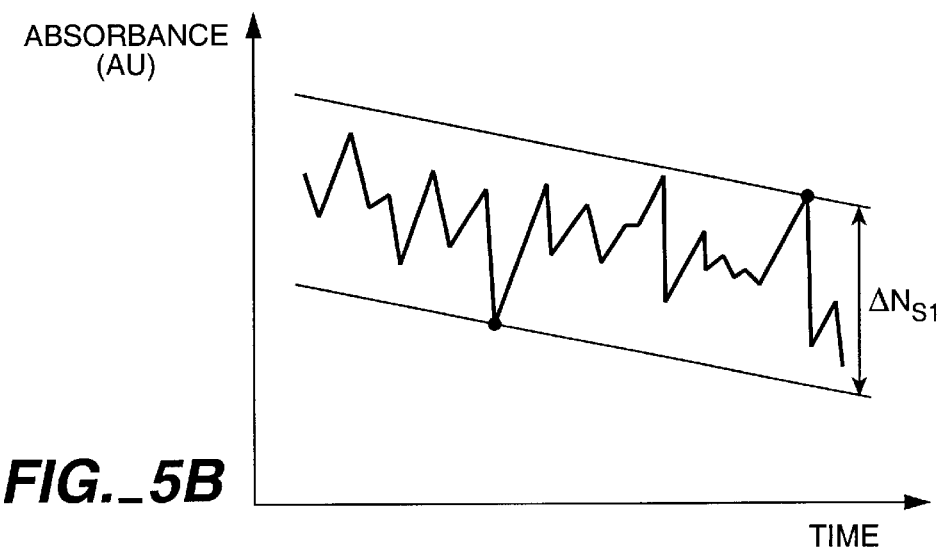
FIG._5B
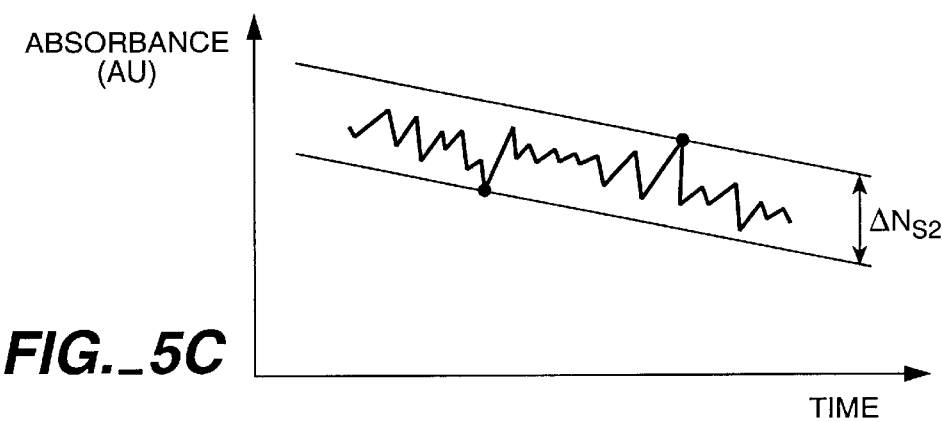
FIG._5C

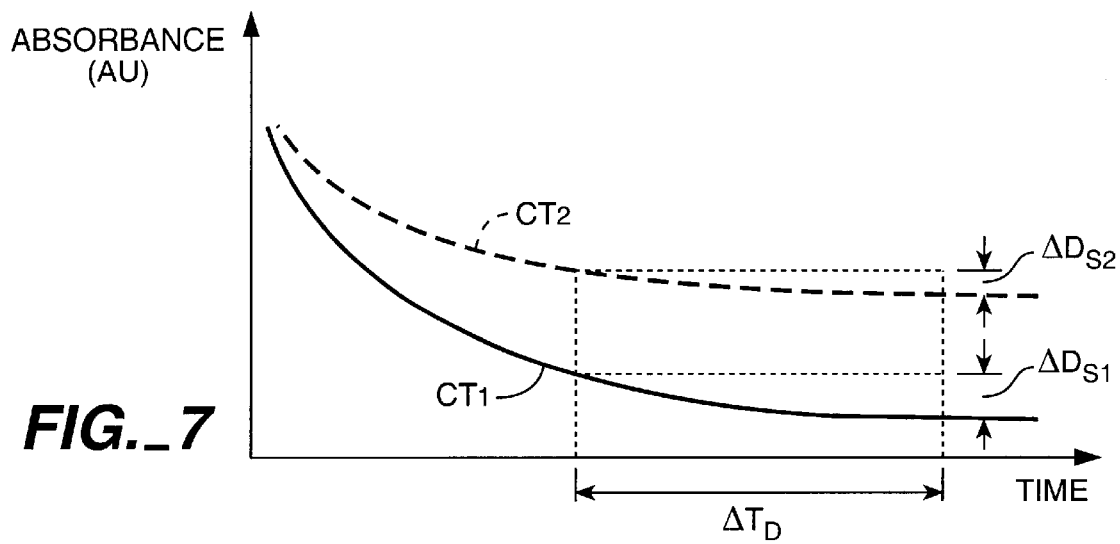
FIG._7
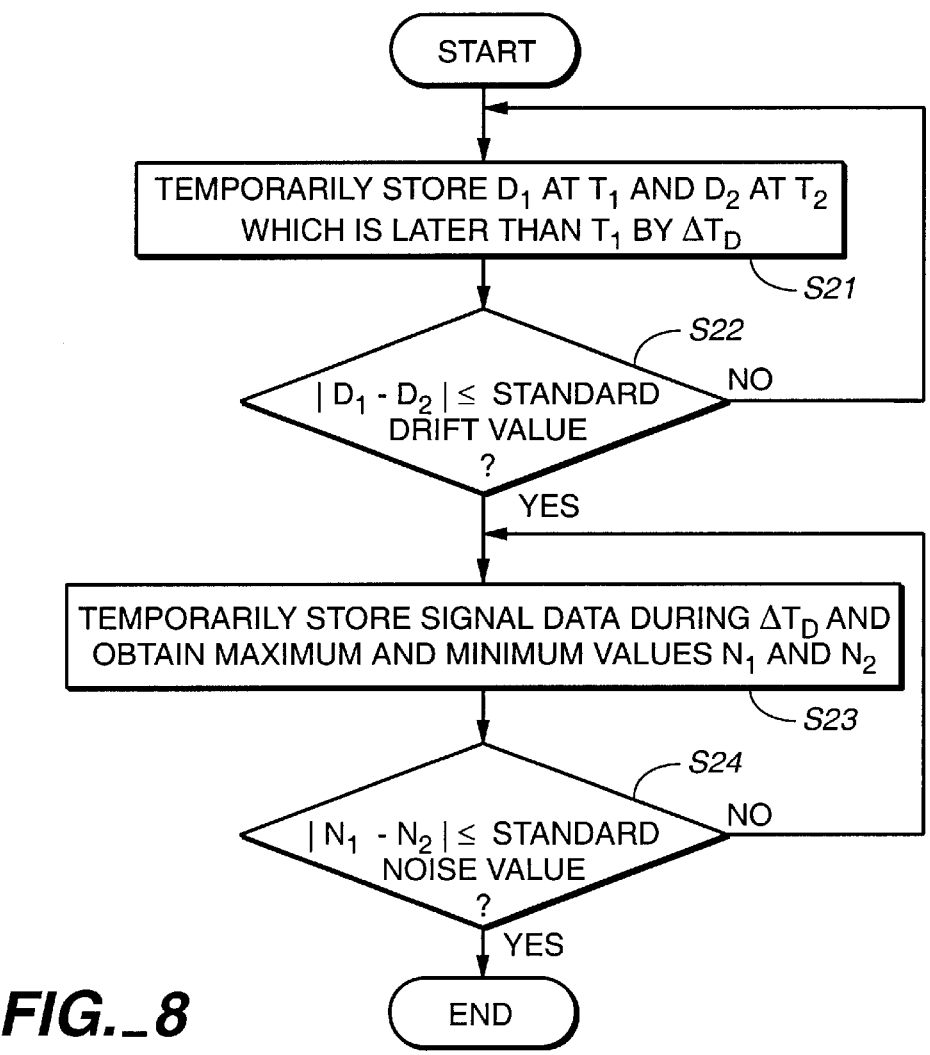
FIG._8

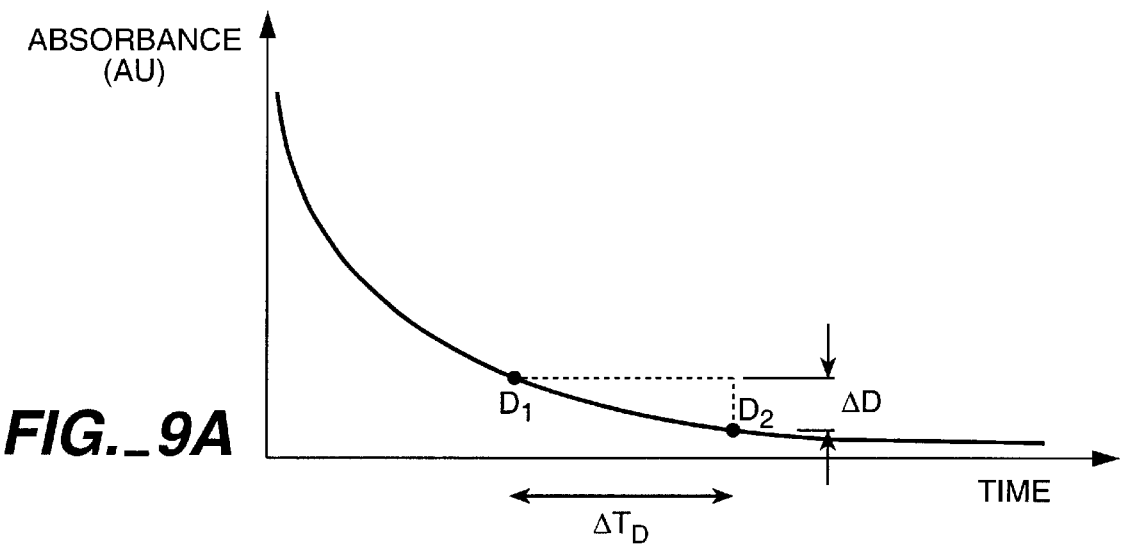
FIG._9A
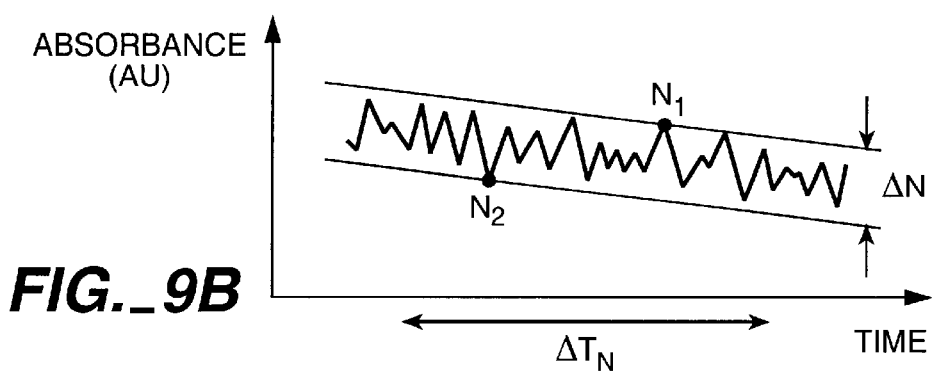
FIG._9B
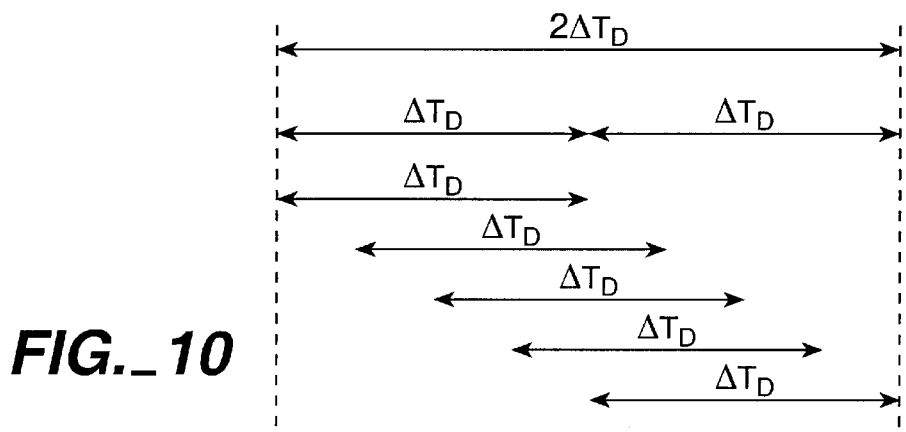
FIG._10

DETECTION DEVICE FOR APPARATUS FOR ANALYSIS

BACKGROUND OF THE INVENTION

This invention relates to a detection device for an apparatus for chromatographic analysis such as a liquid chromatograph.

Detection devices comprising an optical system are commonly used for an apparatus for analysis such as a liquid chromatograph. Such a detection device is adapted to carry out the quantitative analysis of components of a sample by causing the sample separated in a column to pass through a cell together with a solvent, making a beam of light incident on the cell and measuring the light absorbance, the coefficient of refraction or phosphorescence.

When such an apparatus for analysis is used, the operator is required to wait for a significantly long period of time after the power switch for the apparatus is turned on or the source light is switched on until the temperature of the optical system or the light source becomes stabilized such that a reliable analysis can be started. Conventionally, the operator was required to keep watching the screen of a CRT or a plotter display during this wait period. If the operator is distracted or forgets to keep checking, the starting of the analysis may be unwittingly delayed. The same problem is also encountered with gas chromatographs.

SUMMARY OF THE INVENTION

It is therefore an object of this invention to provide a detection device for an apparatus for analysis capable of automatically starting a program of operations for analysis after the power for the apparatus is switched on such that the waste of time for waiting can be eliminated and the burden on the operator can be alleviated.

A detection device embodying this invention for an apparatus for carrying out material, analysis, with which the above and other objects can be accomplished, may be characterized as comprising not only a detector for outputting detection signals but also a stabilization judging, unit for measuring drift and noise of these detection signals overtime automatically and transmitting a start signal which permits the apparatus for analysis to start operations of analysis when the measured drift and noise become smaller than their respective standard values. Such a detection device may preferably further comprise a standard noise value setting unit for receiving detection signals at a detection wavelength while a standard sample is placed inside a detection cell, calculating a standard noise value on the basis of intensity of the detection signals, and transmitting the calculated standard noise value to the stabilization judging unit. If the apparatus for carrying out analysis is a chromatograph, the detection device may preferably further comprise a standard drift value setting unit for storing standard drift values corresponding to temperatures of the column of the chromatograph, retrieving one of stored standard drift values corresponding to measured temperature of the column when measurements are taken by the chromatograph and transmitting the retrieved standard drift value to the stabilization judging unit.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a block diagram of a detection device embodying this invention for an apparatus for analysis;

FIG. 2 is a block diagram of another detection device embodying this invention for an apparatus for analysis;

FIG. 3 is a block diagram of still another detection device embodying this invention for a chromatograph;

FIG. 4 is a flow chart of an example of a program for setting a standard noise value;

FIG. 5A is an example of waveform of an absorption spectrum, and FIGS. 5B and 5C are graphs of noise at different detection wavelengths wherein the vertical axes indicate absorbance measured in AU (Absorbance Unit);

FIG. 7 is a graph showing a drift in detection signals;

FIG. 8 is a flow chart of an example of a program for a wait sequence;

FIGS. 9A and 9B are respectively a graph for showing the drift after the light source is switched on and the noise; and FIG. 10 is a diagram for showing methods of measuring a drift within a given time interval.

DETAILED DESCRIPTION OF THE INVENTION

Figure 6:
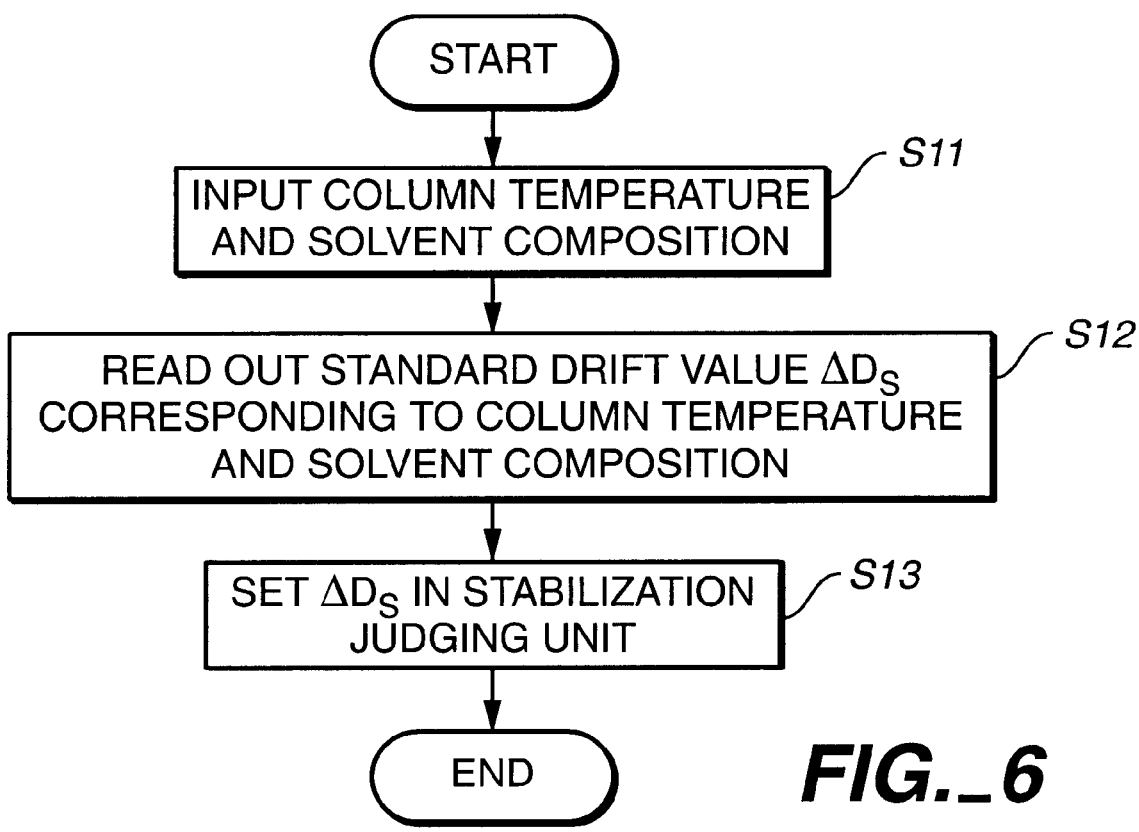
FIG. 6 is a flow chart of an example of a program for setting a standard drift value.

FIG. 1 shows an optical detection device 4 embodying this invention, although the invention is not limited to be applied to detection devices of the optical type. A sample from an apparatus for analysis 2 is transported into a cell inside a sample chamber 6 of the detection device 4. The detection device 4 is provided with a light source 8 and light from this light source 8 is sent into an optical system 10 and is thereby modulated to a desired wavelength. The modulated light beam is then made incident onto the cell inside the sample chamber 6. A detector 12 is provided to detect the light coming out of the cell inside the sample chamber 6. The detector 12 is connected to a stabilization judging unit 14 of which the function is to measure the drift and the noise of detected signals, to judge whether or not the measured drift and noise are smaller than preliminarily set standard values and to transmit to the apparatus for analysis a start signal for starting the analysis if the drift and the noise are determined to be less than the set values. In summary, the drift and the noise are measured for supplying conditions for ending the wait period. As soon as they become below the set values, the start signal is transmitted to the apparatus for analysis 2 and a sequence of steps for the analysis is started. It is preferable that these standard values can be set by the user such that the detection device can be used in an extended field of applications, responding to a variety of needs and purposes of use.

FIG. 2 shows another optical detection device 4' according to another embodiment of this invention, different from the detection device 4 shown in FIG. 1 in that there is a standard noise value setting unit 16 connected to the detector 12 for calculating a standard value for noise ("standard noise value") from the intensity of detection signals at detection wavelengths when a standard sample is deposited in the cell inside the sample chamber 6. The standard noise value setting unit 16 is also connected to the stabilization judging unit 14, to which the calculated standard noise value is transmitted.

The degree of stability in noise required by the detection device is different, depending on the maximum intensity of detected signal at the time of measurement. Thus, if the standard noise value is set too small, the noise will not easily come within the acceptable range (or less than the standard noise value), and a long period of time will be wasted before an analysis can be started. If the standard noise value is made too large, on the other hand, the analysis may be started while intensity of the detected signal is still in an unstable condition, adversely affecting the reproducibility. In other words, it is important to select a standard noise value appropriately, and the judgment of a skilled operator used to be required for this purpose.

According to the embodiment of the invention shown in FIG. 2, the standard noise value setting unit 16 serves to receive detection signals when a standard sample is placed at a specified position of detection, to calculate a standard noise value based on the intensity of the received detection signals and to transmit this calculated standard noise value to the stabilization judging unit 14.

Explained more in detail, a standard sample is placed in the cell inside the sample chamber 6 and the optical system 10 applies light therefrom of a 5 selected detection wavelength. The mutual reaction between this light of incidence and the standard sample is detected by the detector 12, and the detection signals transmitted from the detector 12 are received by the standard noise value setting unit 16. The standard noise value setting unit 16 thereupon automatically calculates a standard noise value on the basis of the intensity of these detection signals and transmits the calculated standard noise value to the stabilization judging unit 14.

With the detection device 4' thus structured, the skill of an experienced operator can be dispensed with, while a suitable standard noise value can be automatically set according to the intensity of the detection signals. This embodiment of the invention is particularly useful in the case of a detection device for detecting the mutual reaction between light and a sample such as the measurement of light absorbance, index of refraction and phosphorescence.

FIG. 3 shows still another optical detection device 4" according to still another embodiment of this invention, different from the detection device 4' shown in FIG. 2 in that it is adapted to be connected to a chromatograph 20 (as an example of apparatus for analysis indicated by numeral 2 in FIG. 2) and that there is a standard drift value setting unit 18 connected to the stabilization judging unit 14 for storing therein standard values of drift ("standard drift values") corresponding to different column temperatures and retrieving a suitable one of the stored standard drift values corresponding to the temperature of the column at the time of a chromatographic measurement.

With a liquid chromatograph, for example, the required degree of stability in drift varies, depending on the temperature of its column and the composition of the solvent. Thus, if a too small standard drift value is set at the time of making measurements, a long period of time will be wasted before an analysis can be started, while if the standard drift value is too large, the analysis may be started before the detection signals have a stabilized intensity, thereby adversely affecting the reproducibility of measured values. In other words, it is also important to select a standard drift value correctly, and the judgment of a skilled operator was required, as was the case with the standard noise value.

According to the embodiment of the invention shown in FIG. 3, data on the column temperature of the liquid chromatograph 20 and/or its solvent composition is inputted to the standard drift value setting unit 18. The time length for measurement of drift is preliminarily set in the standard drift value setting unit 18. Out of the groups of preliminarily inputted data on standard drift values, the standard drift value setting unit 18 serves to retrieve an appropriate standard drift value corresponding to the column temperature and/or the solvent composition. The retrieved standard drift value is transmitted to the stabilization judging unit 14. Such a standard drift value setting unit 18 should also be provided in the case of a gas chromatograph because the drift also depends on the column temperature in the case of a gas chromatograph.

With the detection device 4" thus structured, the skill of an experienced operator can be dispensed with, while a suitable standard drift value can be automatically set according to the column temperature both for a liquid chromatograph and a gas chromatograph and also according to the solvent composition in the case of a liquid chromatograph.

The time length of measurement of the drift need not necessarily be inputted preliminarily to the standard drift value setting unit 18, but may be treated as an variable, adapted to be inputted like the column temperature and/or the solvent composition. The standard drift value and a measured drift value are compared as values per unit time.

The invention is described next by way of a few routines which may be carried out by the devices according to this invention.

FIG. 4 shows an example of a program for setting a standard noise value carried out by the detection device 4" shown in FIG. 3. The program is started after power is switched on for the chromatograph 20 and the detection device 4", the light source 8 is lit up and a standard sample is placed in the cell inside the sample chamber 6. The standard noise value setting unit 16 controls the optical system 10 to carry out a wavelength scan and thereby obtains a spectrum for the standard sample, say, as shown in FIG. 5A as an absorption spectrum (Step S1).

In general, mathematical treatments of detected signals can be carried out with good reproducibility if the noise is less than $\frac{1}{10}$ of the maximum intensity of the detected signals from a sample measurement. Thus, the standard noise value setting unit 16 is set according to this example so as to calculate the standard noise value $\Delta N_S$ as $\frac{1}{10}$ of the absorbance at the detected wavelength (Steps S2 and S3). In other words, the standard noise value $\Delta N_S$ obtained by the standard noise setting unit 16 varies according to the magnitude of the absorbance (or the intensity of the detected signal). If the detected wavelength is $\lambda_1$ in FIG. 5A, the standard noise value is large ($\Delta N_{S1}$) as shown in FIG. 5B but if the detected wavelength is $\lambda_2$ in FIG. 5A, the standard noise value is small ($\Delta N_{S2}$) as shown in FIG. 5C. Although a spectrum of the standard sample is obtained according to this example, the standard noise value $\Delta N_S$ can be calculated from absorbance of the sample. The calculated standard noise value $\Delta N_S$ thus obtained is transmitted to the stabilization judging unit 14 (Step S4).

FIG. 6 shows an example a program for setting a standard drift value carried out by the detection device 4" shown in FIG. 3. The temperature of the column of the chromatograph 20 and the solvent composition are inputted first to the standard drift value setting unit 18 (Step S 11). The time length for the measurement of drift $\Delta T_D$ is assumed to be preliminarily inputted in this example. As shown in FIG. 7, the standard drift value generally varies although the same solvent is used if the column temperature changes. The standard drift value setting unit 18 reads out a suitable standard drift value $\Delta D_S$ in view of the column temperature, the solvent composition and the time length of measurement on the basis of preliminarily inputted data on standard drift values $\Delta D_S$ (Step S12). As shown in FIG. 7, although solvents with the same composition are used for the chromatograph 20 and the time length of measurement $\Delta T_D$ is the same, a relatively larger standard drift value $\Delta D_{S1}$ is required if the column temperature is $CT_1$ but a relatively smaller standard drift value $\Delta D_{S2}$ is required if the column temperature is $CT_2$. The standard drift value $\Delta D_S$ thus read out on the basis of the column temperature, the solvent composition and the time length for drift measurement $\Delta T_D$ is transmitted to the stability judging unit 14 (Step S13).

FIG. 8 shows an example of a program (or the "wait program") for operations both by the detection devices 4 and 4" shown respectively in FIGS. 1 and 3, while waiting for stabilization to set in. In the case of the detection device 4 of FIG. 1, power is switched on both for the apparatus for analysis 2 and the detection device 4, the light source 8 is lit, the optical system 10 is adjusted to transmit light with desired wavelength to the sample chamber 6 and the detector 12 begins to detect the light from the sample chamber 6 before the wait program is started. In the case of the detection device 4" of FIG. 3, the chromatograph 20 is activated, a solvent is caused to flow through the cell inside the sample chamber 6, the optical system 10 is adjusted to transmit light with a desired detection wavelength through the sample chamber 6 and the detector 12 begins to detect light from the sample chamber 6 before the wait program is started.

The stabilization judging unit 14 starts the program by measuring the drift. The value of detection signal $D_1$ from the detector 12 obtained at time $T_1$ after the light source 8 is lit is temporarily stored, and the value of another detection signal $D_2$ obtained at a later time $T_2$ as shown in FIG. 9A is also temporarily stored (Step S21). Drift $\Delta D$ is calculated as the difference between these signal values $D_1$ and $D_2$, or $\Delta D = |D_1 - D_2|$. The time length of drift measurement $\Delta T_D = T_2 - T_1$ such as 60 minutes may be preliminarily set in the standard drift value setting unit 18 in the case of the detection device 4" of FIG. 3. Either in the case of the detection device 4 or 4", the time length of drift measurement $\Delta T_D$ may be variable by an operator.

The drift $\Delta D$ thus calculated is compared with the standard drift value $\Delta D_S$ which has been set (for example, to $3 \times 10^{-10}$ AU/hour) either preliminarily by the user or by the standard drift value setting unit 18. If the drift $\Delta D$ is larger than the standard drift value $\Delta D_S$ (NO in Step S22), the drift is measured again. A new standard drift value may be set by the user.

When the measurements of drift are repeated, they may be repeated such that two periods of successive measurements will not overlap (for example, by carrying out two measurements one after the other, taking a total period of $2\Delta T_D$) or such that successive measurements overlap in time (for example, by carrying out 5 measurements over a period of $2\Delta T_D$), as shown in FIG. 10. By repeating the measurements in mutually (partially and successively) overlapping periods, the wait period can be shortened.

When the drift D becomes smaller than the standard drift value $\Delta D_S$ (YES in Step S22), the measurement of noise is started. Data on the signal detected over a period of noise measurement $\Delta T_N$ (such as 20 seconds, which can be varied by the user) are temporarily stored, and the maximum value $N_1$ and the minimum value $N_2$ are obtained from the stored data, as shown in FIG. 9B, by taking the effects of drift into account (Step S23).

Noise N is determined as the difference between the maximum $N_1$ and the minimum $N_2$ and is compared with a standard noise value $\Delta D_S$ (such as $1 \times 10^{-5}$ AU) which has been set preliminarily either by the user or by the standard noise value setting unit 16. If the noise $\Delta N$ is greater than the standard noise value $\Delta N_S$ (NO in Step S24), the measurements of noise are repeated again. As in the case of repeating the measurements of drift, it is preferable to repeat the measurements of over mutually (partially and successively) overlapping periods $\Delta T_N$ of measurement in order to reduce the total wait period for stabilization.

When the noise $\Delta N$ finally becomes smaller than the standard noise value (YES in Step S24), the stabilization judging unit 14 transmits a signal to the apparatus for analysis 2 (in the case of the detecting device 4 of FIG. 1) or to the chromatograph 20 (in the case of the detecting device 4" of FIG. 3), causing the latter to start its program for carrying out an analysis, if it is ready to do so.

Although the invention has been described above with reference to only a limited number of examples, they are not intended to limit the scope of the invention. Many modifications and variations are possible within the scope of this invention. For example, the conditions for ascertaining stability may be made more stringent by requiring the noise and/or the drift to become smaller than the corresponding standard value more than once. It may also be adapted to output a warning signal if the noise and/or drift failed to become smaller than the corresponding standard value after a specified number of measurements, or within a specified length of time. In summary, this invention makes it unnecessary to depend on the skill of an experienced operator to determine standard noise and/or drift value and hence a waste of wait time can be eliminated.

What is claimed is:

1. A detection device for an apparatus for carrying out materials analysis, said detection device comprising:
    a detector for outputting detection signals; and
    a stabilization judging unit for measuring drift and noise of said detection signals over time and automatically transmitting a start signal which permits said apparatus to start said analysis when the measured drift becomes smaller than a standard drift value and the measured noise becomes smaller than a standard noise value.

2. The detection device of claim 1 further comprising:
    a detection cell; and
    a standard noise value setting means unit for receiving detection signals at a detection wavelength while a standard sample is placed inside said detection cell, calculating a standard noise value on the basis of intensity of said detection signals as one-tenth of the optical absorbance measured for spectrum of an analyzed sample at said detection wavelength, and transmitting said calculating standard noise value to said stabilization judging unit.

3. The detection device of claim 1 wherein said apparatus is a chromatograph having a column, said detection device further comprising a standard drift value setting unit for storing standard drift values corresponding to temperatures of said column, retrieving one of said stored standard drift values corresponding to measured temperature of said column when measurements are taken by said detection device and transmitting the retrieved standard drift value to said stabilization judging unit.

4. The detection device of claim 2 wherein said apparatus is a chromatograph having a column, said detection device further comprising a standard drift value setting unit for storing standard drift values corresponding to temperatures of said column, retrieving one of said stored standard drift values corresponding to measured temperature of said column when measurements are taken by said detection device and transmitting the retrieved standard drift value to said stabilization judging unit.

5. The detection device of claim 1 further comprising means for storing a time length for measuring noise.

6. The detection device of claim 2 further comprising means for storing a time length for measuring noise.

7. The detection device of claim 3 further comprising means for storing a time length for measuring noise.

8. The detection device of claim 4 further comprising means for storing a time length for measuring noise.

9. The detection device of claim 1 further comprising means for storing a time length for measuring drift.

10. The detection device of claim 2 further comprising means for storing a time length for measuring drift.

11. The detection device of claim 3 further comprising means for storing a time length for measuring drift.

12. The detection device of claim 4 further comprising means for storing a time length for measuring drift.

\* \* \* \* \*